(12) United States Patent
Wood et al.

(10) Patent No.: US 10,221,441 B1
(45) Date of Patent: Mar. 5, 2019

(54) COMPOUNDS AND METHODS FOR ASSAYING ACTIVITY OF LYSOSOMAL STORAGE DISEASES

(71) Applicant: Cambridge Isotope Laboratories, Inc., Andover, MA (US)

(72) Inventors: William Wakefield Wood, Andover, MA (US); Jeffery Allen Gladding, Burlington, MA (US)

(73) Assignee: Cabridge Isotope Laboratories, Inc., Tewksbury, MA (US)

( * ) Notice: Subject to any disclaimer, the term of this patent is extended or adjusted under 35 U.S.C. 154(b) by 0 days.

(21) Appl. No.: 15/837,900

(22) Filed: Dec. 11, 2017

(51) Int. Cl.
| | |
|---|---|
| *C07D 311/08* | (2006.01) |
| *C12Q 1/25* | (2006.01) |
| *C12Q 1/40* | (2006.01) |
| *C07D 311/16* | (2006.01) |
| *C07H 17/075* | (2006.01) |

(52) U.S. Cl.
CPC .............. *C12Q 1/40* (2013.01); *C07D 311/16* (2013.01); *C07H 17/075* (2013.01); *C12Y 302/01076* (2013.01); *G01N 2333/924* (2013.01); *G01N 2496/00* (2013.01); *G01N 2800/042* (2013.01)

(58) Field of Classification Search
CPC ................................ C07D 311/08; C12Q 1/25
USPC ................................................ 549/399; 435/4
See application file for complete search history.

(56) References Cited

PUBLICATIONS

Fernandes, M.J.G. et al.: Comparative study of polyaromatic and heteroaromatic fluorescent photocleavable protecting groups. Tetrahedron, vol. 64, pp. 3032-3038, 2008.*

* cited by examiner

*Primary Examiner* — Charanjit Aulakh
(74) *Attorney, Agent, or Firm* — Foley & Lardner LLP

(57) ABSTRACT

A compound having the formula:

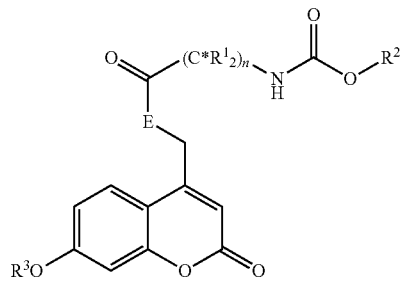

wherein each $R^1$ is independently H or D; $R^2$ is alkyl or cycloalkyl; $R^3$ is a H, alkyl, cycloalkyl, heterocycloalkyl, or carboxylate; E is $NR^4$ or O; $R^4$ is H or alkyl; n is an integer from 1 to 20; and C* represents a natural distribution of $^{12}C$ and $^{13}C$, or enrichment with $^{13}C$.

19 Claims, No Drawings

COMPOUNDS AND METHODS FOR ASSAYING ACTIVITY OF LYSOSOMAL STORAGE DISEASES

FIELD

The present technology is generally related to compounds for assaying lysosomal storage diseases such as mucopolysaccharidosis-1 ("MPS-1").

SUMMARY

In one aspect, a compound has the formula:

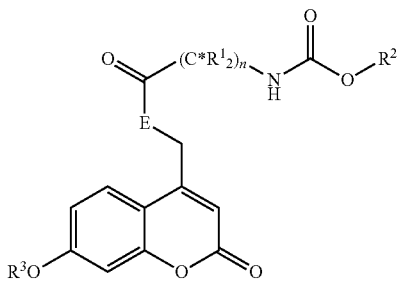

wherein each $R^1$ is independently H or D; $R^2$ is alkyl; $R^3$ is a H, alkyl, cycloalkyl, heterocycloalkyl, or carboxylate; E is $NR^4$ or O; $R^4$ is H or alkyl; n is an integer from 1 to 20; and $C^*$ represents a natural distribution of $^{12}C$ and $^{13}C$, or enrichment with $^{13}C$.

In another aspect, a method is provided for assaying α-L-iduronidase enzymatic activity, the method includes contacting an α-L-iduronidase substrate with α-L-iduronidase for a pre-determined time to provide a solution comprising an α-L-iduronidase product; contacting the α-L-iduronidase with an α-L-iduronidase internal standard before, simultaneously with, or after contacting the α-L-iduronidase substrate with α-L-iduronidase to provide a solution comprising the α-L-iduronidase product and α-L-iduronidase internal standard, extracting the solution comprising the α-L-iduronidase product and α-L-iduronidase internal standard with an organic solvent to provide an organic phase that includes the α-L-iduronidase product and α-L-iduronidase internal standard; and determining the quantity of the α-L-iduronidase product. In such a process, the internal standard has the formula:

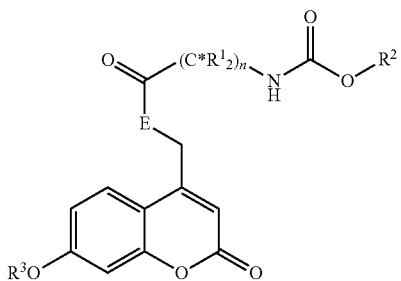

wherein each $R^1$ is independently H or D; $R^2$ is alkyl; $R^3$ is a H, alkyl, cycloalkyl, or carboxylate; E is $NR^4$ or O; $R^4$ is H or alkyl; n is an integer from 1 to 20; and $C^*$ represents a natural distribution of $^{12}C$ and $^{13}C$, or enrichment with $^{13}C$; and wherein the substrate has the formula:

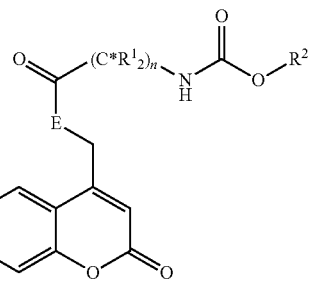

wherein each $R^1$ is independently H or D; $R^2$ is alkyl; $R^3$ is a cycloalkyl, heterocycloalkyl, or carboxylate; E is $NR^4$ or O; $R^4$ is H or alkyl; n is an integer from 1 to 20; and $C^*$ represents a natural distribution of $^{12}C$ and $^{13}C$, or enrichment with $^{13}C$, wherein the substrate and the internal standard not the same.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a perhaloalkyl group.

As used herein, "heterocycloalkyl" groups are cyclic alkyl groups in which a heteroatom (i.e. O, S, or N) is included within the ring structure.

The compounds and methods described herein are for assaying lysosomal storage diseases. The lysosomal storage disease may be, in some embodiments, MPS-1, otherwise known as Hurler Disease or Hurler Syndrome.

In one aspect, a compound is provided having the formula:

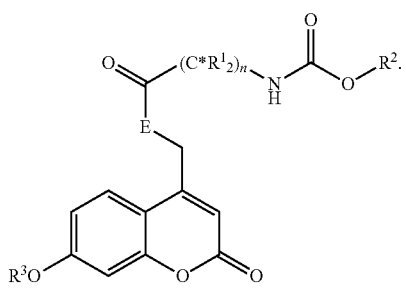

In the formula each $R^1$ is independently H or D; $R^2$ is H, alkyl, or cycloalkyl; $R^3$ is a H, alkyl, cycloalkyl, heterocycloalkyl, or carboxylate; E is $NR^4$ or O; $R^4$ is H or alkyl; n is an integer from 1 to 20; and C* represents a natural distribution of $^{12}C$ and $^{13}C$, or enrichment with $^{13}C$. As used herein, a "natural distribution of $^{12}C$ and $^{13}C$" is understood to mean a naturally occurring distribution without enrichment with $^{13}C$. In any of the above embodiments, $R^3$ may be H or heterocycloalkyl. In any of the above embodiments, E may be NH. In any of the above embodiments, $R^3$ may be a heterocycloalkyl group of formula:

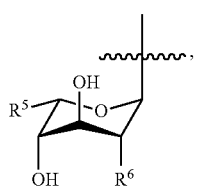

wherein $R^5$ and $R^6$ are each independently —OH, —CO(O)X, or —OSO$_3$X, and X is H, Li$^+$, Na$^+$, K$^+$, or [NR$^4$]$^+$. In any of the above embodiments, $R^2$ may be a $C_3$-$C_6$ alkyl. In any of the above embodiments, $R^5$ may be OH and $R^6$ may be OH. In any of the above embodiments, $R^5$ may be —CO(O)X, $R^6$ may be —OSO$_3$X, and X is H. In some embodiments, $R^5$ is —CO(O)H and $R^6$ is OH. In any of the above embodiments, $R^2$ may isopropyl or t-butyl. In any of the above embodiments, n may be an integer from 3 to 12. In any of the above embodiments, n may be 3.

In some embodiments, the compound may be referred to as a "substrate" where $R^3$ is a heterocycloalkyl group of formula:

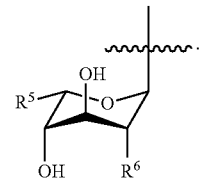

In some embodiments, the compound may be referred to as an "internal standard" where $R^3$ is H. In addition when comparing a "substrate" and the corresponding "internal standard," n in the "substrate," is n−1 in the: internal standard."

In some embodiments, the compound is A, B, or C:

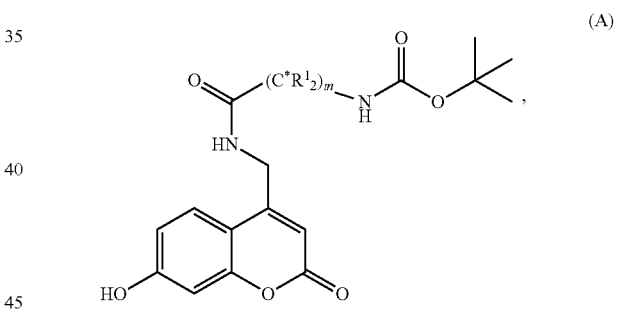

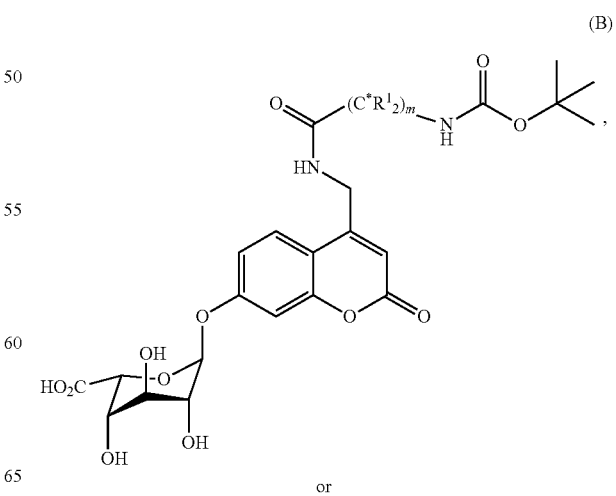

or

-continued

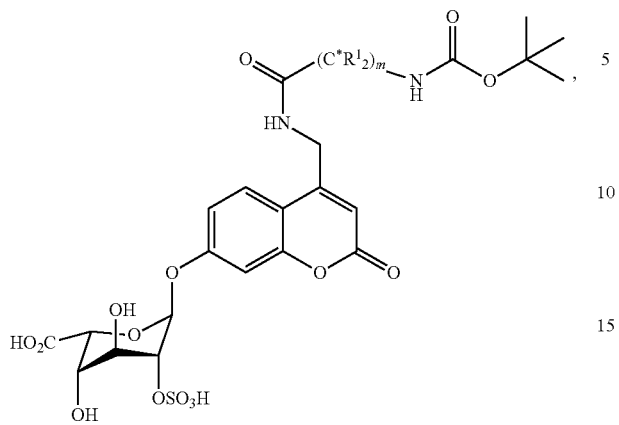

(C)

where each $R^1$ is independently H or D; and m is 3 or 4. In some embodiments, in compound (A), m is 3. In some other embodiments, in compound (B) or (C), m is 4.

In another aspect, a method is provided for assaying α-L-iduronidase enzymatic activity. The method includes contacting an α-L-iduronidase substrate with α-L-iduronidase for a pre-determined time to provide a solution comprising an α-L-iduronidase product; contacting the α-L-iduronidase with an α-L-iduronidase internal standard before, simultaneously with, or after contacting the α-L-iduronidase substrate with α-L-iduronidase to provide a solution comprising the α-L-iduronidase product and α-L-iduronidase internal standard, wherein the internal standard has the formula above; extracting the solution comprising the α-L-iduronidase product and α-L-iduronidase internal standard with an organic solvent to provide an organic phase that includes the α-L-iduronidase product and α-L-iduronidase internal standard; and determining the quantity of the α-L-iduronidase product. In some embodiments, the solution comprising α-L-iduronidase is obtained by contacting a sample containing α-L-iduronidase with a first buffer solution. The sample may be a blood sample. In some embodiments where the same is a blood sample, the sample is a dried blood spot from a newborn screening card.

The substrate may have the formula:

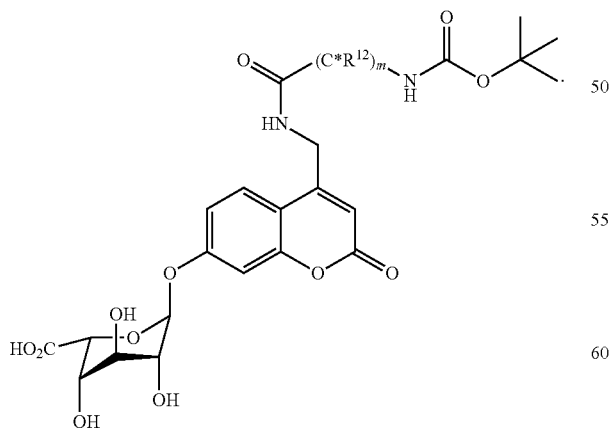

In the formula, where each $R^1$ is independently H or D; and m is an integer from 1 to 20. In some embodiments, m is an integer from 2 to 12. In some embodiments, m is 4.

The internal standard may have the formula:

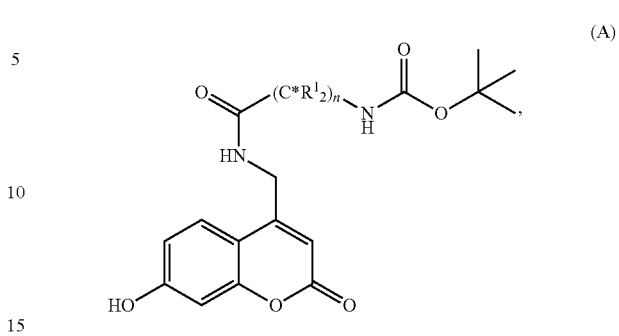

(A)

where each $R^1$ is independently H or D; and n is from 2 to 12. In some embodiments, n is 3. In some embodiments, n is equal to m−1.

The compounds described herein may be used in a variety of additional assaying methods for MPS-1. Such additional assaying methods are described, for example, in Scott et. al. *J. Pediatrics* (2013) 163(2):498-503; Blanchard et al. *Clin. Chem.* (2008) 54(12):2067-2070; Wang et. al. (2005) 51(5): 898-900; and U.S. Patent Publication No. 2014/0249054.

The present invention, thus generally described, will be understood more readily by reference to the following examples, which are provided by way of illustration and are not intended to be limiting of the present invention.

EXAMPLES

General 1.

The synthesis of the MPS-1 internal standard is generally described in Scheme 1. The specific processes are further described below.

Scheme 1:

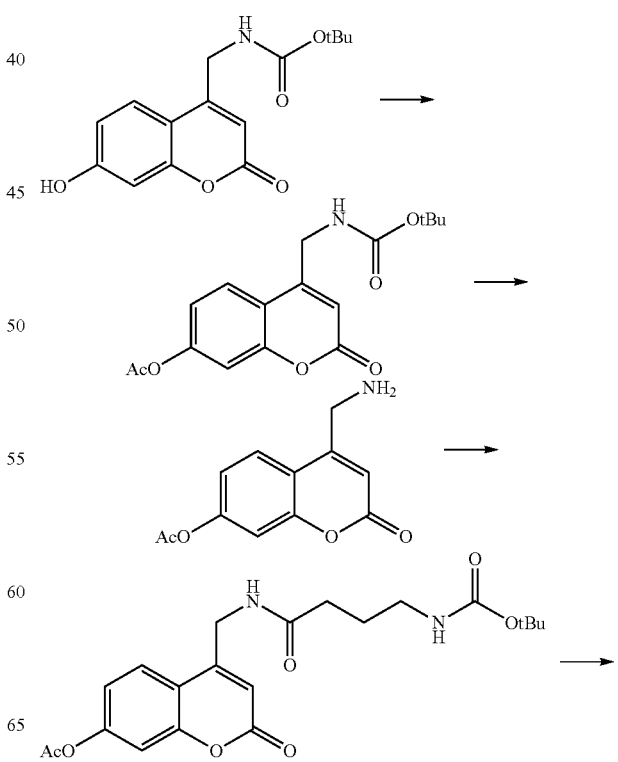

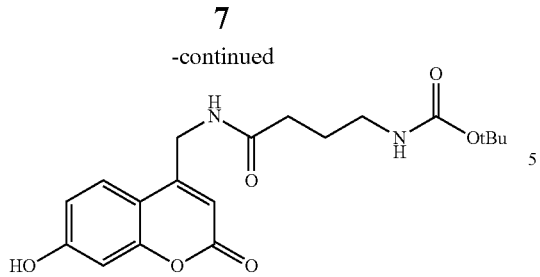

Example 1. The Synthesis of 4-(((tert-butoxycarbonyl)amino)methyl)-2-oxo-2H-chromen-7-yl acetate

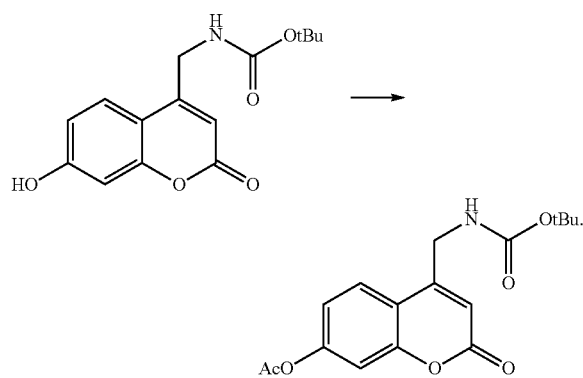

To a suspension of tert-butyl-((7-hydroxy-2-oxo-2H-chromen-4-yl)methyl)carbamate (32.5 g, 111.6 mmol) in anhydrous dichloromethane (558 mL) under nitrogen was added anhydrous pyridine (19.0 mL, 234.3 mmol). The suspension was cooled in an ice bath and acetic anhydride (21.1 mL, 223.1 mmol) was added dropwise over 5 minutes. After 3.5 hours the organic solution was washed with aqueous hydrochloric acid (1M, 2×100 mL). The combined aqueous washes were extracted with dichloromethane (100 mL). The combined organic layer was washed with saturated sodium bicarbonate (100 mL) and dried over magnesium sulfate. The residue was crystallized from hot ethyl acetate and hexanes to afford of 4-(((tert-butoxycarbonyl)amino)methyl)-2-oxo-2H-chromen-7-yl acetate (26.2 g, 70%). A second crop of product was similarly obtained from the filtrate to yield additional product (9.3 g, 25%). $^1$H NMR (500 MHz, CDCl$_3$) δ 7.62 (d, 1H), 7.14 (s, 1H), 7.08 (d 1H), 6.39 (s, 1H), 4.90 (bs, 1H), 4.50 (d, 2H), 2.34 (s, 3H), 1.48 (s, 9H).

Example 2. The Synthesis of 4-(aminomethyl)-2-oxo-2H-chromen-7-yl acetate

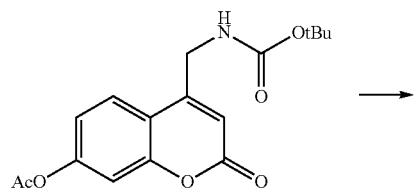

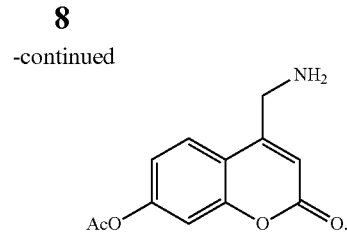

To a solution of 4-(((tert-butoxycarbonyl)amino)methyl)-2-oxo-2H-chromen-7-yl acetate (35.4 g, 106.2 mmol) in dichloromethane (266 mL) was added 1,3-dimethoxybenzene (83.5 mL, 637.4 mmol) and trifluoroacetic acid (266 mL). After 30 minutes the reaction was concentrated and the residue partitioned between water (100 mL) and diethyl ether (100 mL). A solid material precipitated from the solution and was collected via filtration. The layers of the filtrate were separated and the aqueous washed with diethyl ether (100 mL). The combined organic layer was extracted with aqueous hydrochloric acid (1M, 2×50 mL). The solid material was suspended in the combined aqueous layer and neutralized to pH=8 with saturated sodium bicarbonate. A precipitate formed and was allowed to sir overnight at room temperature. The solid was collected via filtration, washed with diethyl ether (3×100 mL), and dried to afford 4-(aminomethyl)-2-oxo-2H-chromen-7-yl acetate (21.5 g, 87%). $^1$H NMR (300 MHz, DMSO-d$_6$) δ 8.42 (t, 2H), 7.63 (d, 1H), 6.79 (d, 1H), 6.72 (s 1H), 6.02 (s, 1H), 4.41 (d, 2H), 1.93 (s, 3H).

Example 3. The Synthesis of tert-butyl (4-(((7-hydroxy-2-oxo-2H-chromen-4-yl)methyl)amino)-4-oxobutyl)carbamate

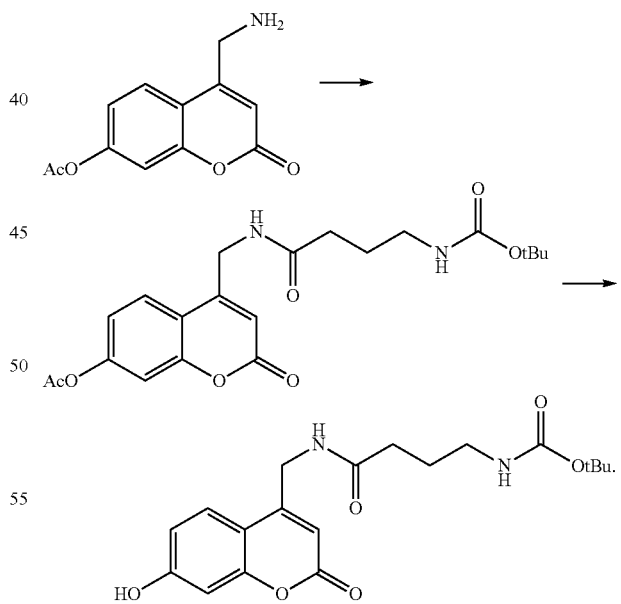

To a 0° C. solution of 4-((tert-butoxycarbonyl)amino) butanoic acid (18.8 g, 92.3 mmol) in anhydrous tetrahydrofuran (462 mL) was added hydroxybenzotriazole monohydrate (15.6 g, 101.6 mmol) and 1-(3-dimethylaminopropyl)-3-ethylcabodiimide hydrochloride (19.5 g, 101.6 mmol). The reaction was allowed to stir for 30 minutes. A suspension of 4-(aminomethyl)-2-oxo-2H-chromen-7-yl acetate (21.5 g, 92.3 mmol) in anhydrous N,N-dimethylformamide (180 mL) was added over 20 minutes. The reaction was allowed to warm to room temperature and stir for 36 hours. The reaction was concentrated and the residue partitioned between ethyl acetate (400 mL) and water (150 mL). The layers wee there separated and the organic was washed with water (100 mL), aqueous hydrochloric acid (1M, 2×75 mL), saturated sodium bicarbonate (2×50 mL), and brine (50 mL). The organic layer was dried over magnesium sulfate and concentrated. The residue was dissolved in methanol (350 mL) and aqueous sodium hydroxide (2N, 60 mL) added. After 30 minutes the methanol was removed in vacuo and the solution cooled in an ice bath. The pH was adjusted to pH=5 with aqueous hydrochloric acid (1M) and the aqueous solution extracted with 9:1 dichloromethane:methanol (3×100 mL). A precipitate was removed via filtration, dissolved in methanol, and added to the organic layer. The aqueous filtrate was extracted with chloroform (2×100 mL). The combined organic layer was dried over magnesium sulfate, filtered, and concentrated. The residue was then partitioned between ethyl acetate (400 mL) and aqueous hydrochloric acid (1M, 100 mL). The layers were separated and the organic washed with aqueous hydrochloric acid (1M, 4×100 mL), water (100 mL), and brine (100 mL). The organic layer was dried over magnesium sulfate, filtered, and concentrated. The residue was purified via column chromatography on silica gel (ethyl acetate, then 1% methanol in ethyl acetate) to afford tert-butyl (4-(((7-hydroxy-2-oxo-2H-chromen-4-yl)methyl)amino)-4-oxobutyl)carbamate (10.2 g, 29%). $^1$H NMR (400 MHz, MeOH-d$_4$) δ 7.61 (d, 1H), 6.82 (d, 1H), 6.66 (s 1H), 6.04 (s, 1H), 4.47 (s, 2H), 3.04 (t, 2H), 2.26 (t, 2H), 1.81 (dd, 2H), 1.42 (s, 9H). $^{13}$C NMR (75.4 MHz, MeOH-D$_4$) δ 175.85, 163.64, 163.07, 158.57, 156.76, 154.93, 126.58, 114.44, 111.75, 109.13, 103.70, 80.00, 40.82, 40.44, 34.16, 28.77, 27.29.

General 2.

The synthesis of the MPS-1 substrate is generally described in Scheme 2. The specific processes are further described below.

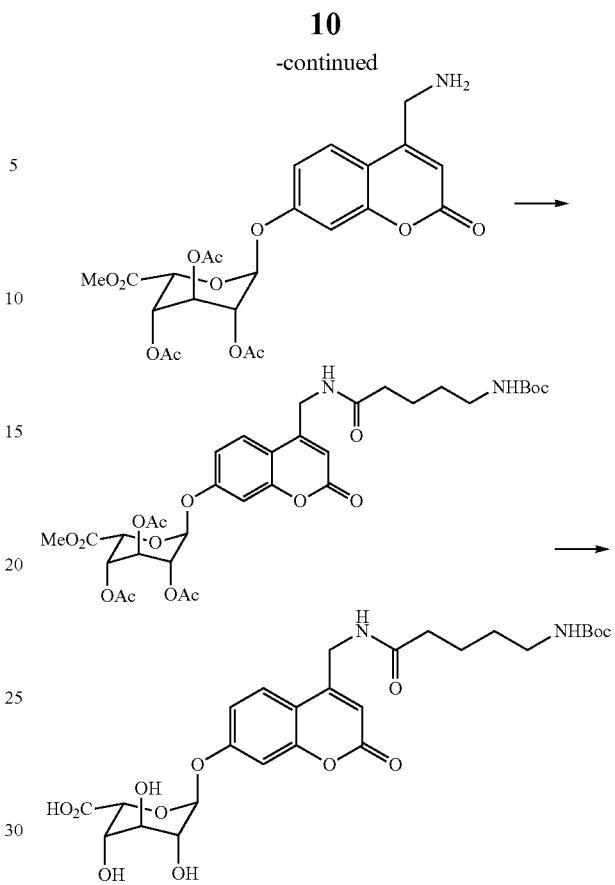

Example 4. The Synthesis of ((7-hydroxy-2-oxo-2H-chromen-4-yl)methyl) carbamate

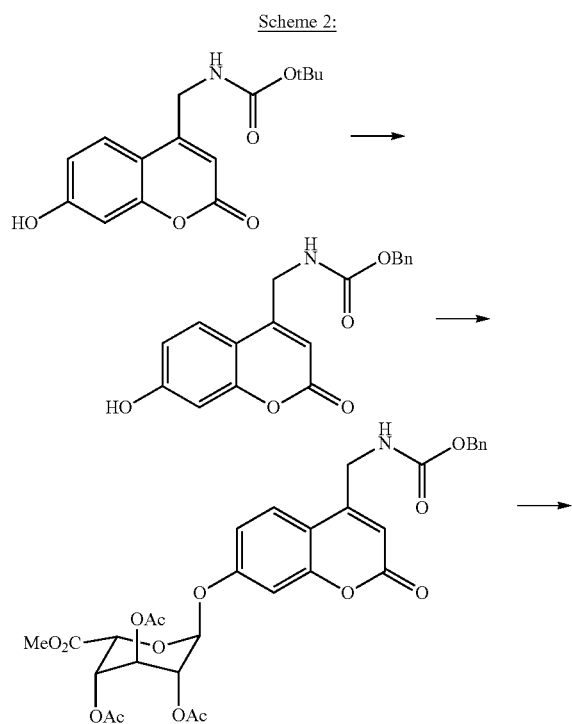

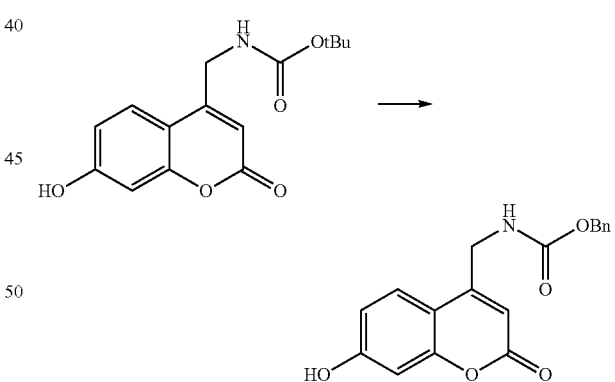

To a suspension of tert-butyl ((7-hydroxy-2-oxo-2H-chromen-4-yl)methyl)carbamate (6.9 g, 23.7 mmol) in dichloromethane (59 mL) was added trifluoroacetic acid (59 mL). The resulting solution was stirred at room temperature for 30 minutes. Toluene (100 mL) was added and the reaction concentrated in vacuo. The resulting white solid was suspended in saturated aqueous sodium bicarbonate (71 mL). A solution of N-(benzyloxycarbonyloxy)succinimide (6.2 g, 24.9 mmol) in THF (95 mL) was added and the reaction stirred at room temperature for 15 hours. Diethyl ether (100 mL) was added and the layers were separated. The aqueous layer was extracted with diethyl ether (2×100 mL) and the combined washes were then washed with brine, dried over magnesium sulfate, filtered, and concentrated. The residue was purified via column chromatography on silica gel (0 to 100% ethyl acetate in hexanes) to afford ((7-hydroxy-2-oxo-2H-chromen-4-yl)methyl)carbamate (7.25 g, 94%). $^1$H NMR (300 MHz, MeOH-d$_4$) δ 7.61 (d, 1H), 7.50-7.20 (m, 5H), 6.81 (d, 1H), 6.71 (s 1H), 6.12 (s, 1H), 5.13 (s, 2H), 4.50 (s, 2H).

Example 5. The Synthesis of methyl-1-((4-((((benzyloxy)carbonyl)amino)methyl)-2-oxo-2H-chromen-7-yl)oxy)-2,3,4-triacetyl alpidopyranuronate

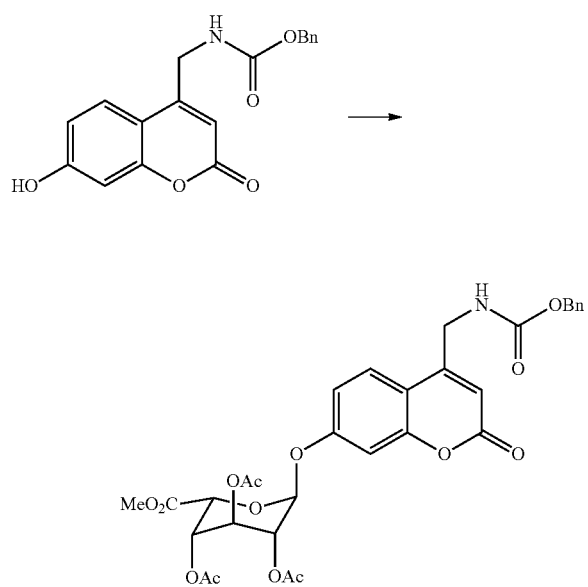

To a suspension of benzyl ((7-hydroxy-2-oxo-2H-chromen-4-yl)methyl)carbamate (5.98 g, 18.4 mmol) in anhydrous dichloromethane (74 mL) was added N,O-bis(trimethylsilyl)acetamide (5.4 mL, 22.0 mmol) dropwise and the reaction stirred at room temperature for 30 minutes. The resulting solution was transferred via cannula to a solution of methyl 1-deoxy-1-fluoro-2,3,4-triacetyl alpidopyranuronate (4.95 g, 14.7 mmol) in anhydrous dichloromethane (74 mL). The solution was cooled in an ice batch and boron trifluoride diethyl etherate (5.44 mL, 44.1 mmol) added dropwise over 3 minutes. The reaction was allowed to warm slowly to room temperature. After 6 hours saturated aqueous sodium bicarbonate (100 mL) was added. The layers were separated and the aqueous extracted with dichloromethane (2×100 mL). The combined organic was dried over magnesium sulfate, filtered, and concentrated. The residue was purified via chromatography on silica gel (50% ethyl acetate/hexanes) to afford methyl-1-((4-((((benzyloxy)carbonyl)amino)methyl)-2-oxo-2H-chromen-7-yl)oxy)-2,3,4-triacetyl alpidopyranuronate (8.4 g, 89%). $^1$H NMR (300 MHz, CDCl$_3$) δ 7.53 (d, 1H), 7.45-7.15 (m, 5H), 7.07 (s, 1H), 7.01 (d, 1H), 6.30 (s 1H), 5.85 (s, 1H), 5.21 (s, 2H), 5.16 (s, 2H), 5.05 (s, 1H), 4.90 (s, 1H), 4.54 (d, 2H), 3.78 (s, 3H), 2.18 (s, 3H) 2.12 (s, 3H), 2.11 (s, 3H).

Example 6. The Synthesis of methyl-1-((4-((amino)methyl)-2-oxo-2H-chromen-7-yl)oxy)-2,3,4-triacetyl alpidopyranuronate

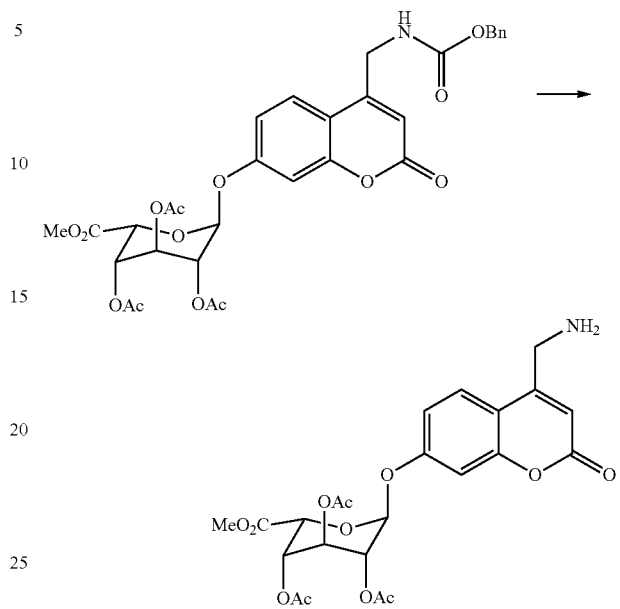

To a solution of methyl-1-((4-((((benzyloxy)carbonyl)amino)methyl)-2-oxo-2H-chromen-7-yl)oxy)-2,3,4-triacetyl alpidopyranuronate (13.0 g, 20.3 mmol) in ethyl acetate (51 mL) and ethanol (51 mL) was added ammonium formate (12.8 g, 202.6 mmol). The resulting mixture was degassed by bubbling nitrogen through for 20 minutes before adding 10% palladium on carbon Degussa type E101 (2.16 g). After 4 hours the reaction was filtered through celite and the filter cake washed with ethyl acetate (50 mL) and ethanol (50 mL). The filtrate was concentrated and the residue purified via chromatography on silica gel (5% methanol in dichloromethane to 7.5% methanol in dichloromethane with 0.1% triethylamine) to afford approximately 90% pure methyl-1-((4-((amino)methyl)-2-oxo-2H-chromen-7-yl)oxy)-2,3,4-triacetyl alpidopyranuronate (8.4 g, 81% yield). $^1$H NMR (400 MHz, CDCl$_3$) δ 7.55 (d, 1H), 7.06 (s, 1H), 7.02 (d, 1H), 6.47 (s 1H), 5.86 (s, 1H), 5.20 (s, 2H), 5.04 (s, 1H), 4.90 (s, 1H), 4.04 (s, 2H), 3.80 (s, 3H), 2.20 (s, 3H) 2.12 (s, 3H), 2.11 (s, 3H).

Example 7. The Synthesis of methyl-1-((4-((5-((tert-butoxycarbonyl)amino)pentanamido)methyl)-2-oxo-2H-chromen-7-yl)oxy)-2,3,4-triacetyl alpidopyranuronate

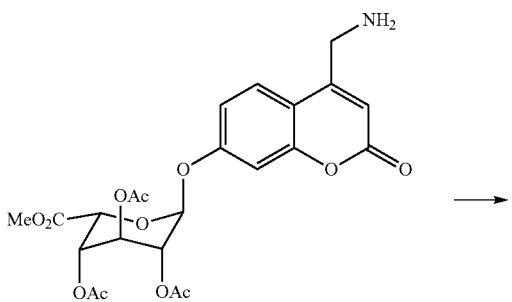

-continued

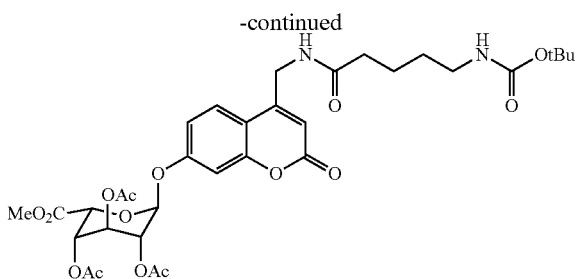

To a 0° C. solution of 5-aminovaleric acid (4.0 g, 18.4 mmol) in anhydrous tetrahydrofuran (83.8 mL) was added 1-hydroxybenzotriazole monohydrate (3.08 g, 20.1 mmol) and (1-(3-dimethylaminopropyl)-3-ethylcabodiimide hydrochloride (3.85 g, 20.1 mmol). A solution of methyl 1-((4-((amino)methyl)-2-oxo-2H-chromen-7-yl)oxy)-2,3,4-triacetyl alpidopyranuronate (8.5 g, 16.8 mmol) in anhydrous N,N-dimethylformamide (35 mL) was added to the reaction dropwise. The reaction was allowed to warm to room temperature overnight. The reaction was concentrated in vacuo and the residue partitioned between water (100 mL) and ethyl acetate (200 mL). The layers were separated and the aqueous extracted with ethyl acetate (2×100 mL). The combined organic was washed twice with 1M hydrochloric acid (50 mL), saturated sodium bicarbonate (50 mL), and brine (50 mL). The organic layer was dried over magnesium sulfate and the residue purified via chromatography on silica gel (EtOAc). This material was further purified via chromatography on silica gel (0 to 10% methanol in dichloromethane) to afford methyl-1-((4-((5-((tert-butoxycarbonyl)amino)pentanamido)methyl)-2-oxo-2H-chromen-7-yl)oxy)-2,3,4-triacetyl alpidopyranuronate (2.75 g, 23%). $^1$H NMR (300 MHz, CDCl$_3$) δ 7.57 (d, 1H), 7.06 (s, 1H), 7.02 (d, 1H), 6.48 (bt, 1H), 6.21 (s, 1H), 5.84 (s, 1H), 5.21 (s, 1H), 5.06 (s, 1H), 4.91 (s, 1H), 4.71 (bt, 1H), 4.57 (d, 2H), 3.77 (s, 3H), 3.14 (quart., 2H), 2.34 (t, 2H), 2.18 (s, 3H) 2.12 (s, 3H), 2.11 (s, 3H), 1.80-1.62 (m, 2H), 1.61-1.45 (m, 2H), 1.40 (s, 9H).

Example 8. The Synthesis of 1-((4-((5-((tert-butoxycarbonyl)amino)pentanamido)methyl)-2-oxo-2H-chromen-7-yl)oxy) alpidopyranuronate

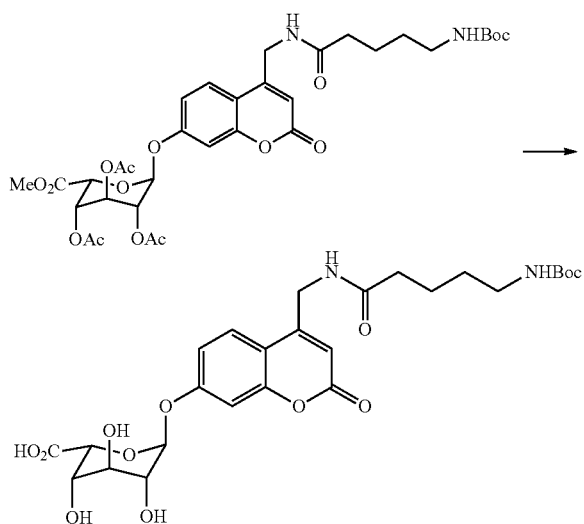

To a 0° C. solution of methyl-1-((4-((5-((tert-butoxycarbonyl)amino)pentanamido)methyl)-2-oxo-2H-chromen-7-yl)oxy)-2,3,4-triacetyl alpidopyranuronate (2.75 g, 3.89 mmol) in methanol (19.5 mL) was added a solution of lithium hydroxide (1M, 19.45 mL). The reaction was allowed to warm slowly to room temperature. After 6 hours a 2$^{nd}$ portion of lithium hydroxide (0.09 g, 3.9 mmol) was added and the reaction was stirred at room temperature for 16 hours. A 3$^{rd}$ portion of lithium hydroxide (0.09 g, 3.9 mmol) was added and the reaction stirred for an additional 24 hours. The methanol was removed in vacuo and the aqueous layer brought to pH=4 with 1N hydrochloric acid. The aqueous layer was concentrated and the residue purified on reverse phase silica, eluting with 10 to 100% methanol in water to afford 1-((4-((5-((tert-butoxycarbonyl)amino)pentanamido)methyl)-2-oxo-2H-chromen-7-yl)oxy) alpidopyranuronate (0.61 g, 28% yield). $^1$H NMR (400 MHz, MeOH-D$_4$) δ 7.70 (d, 1H), 7.52 (s, 1H), 7.46 (d, 1H), 6.14 (s, 1H), 5.59 (d, 1H), 4.57 (s, 2H), 4.38 (d, 1H), 3.71 (dd, 1H), 3.61 (dd, 1H), 3.48 (dd, 1H), 3.08 (t, 2H) 2.32 (t, 2H), 1.76-1.60 (m, 2H), 1.60-1.43 (m, 2H), 1.41 (s, 9H). $^{13}$C NMR (75.4 MHz, MeOH-D$_4$) δ176.29, 163.32, 162.29, 158.58, 156.30, 154.58, 126.23, 115.09, 113.56, 110.42, 105.34, 99.26, 79.79, 74.67, 74.01, 73.57, 72.51, 40.89, 40.46, 36.52, 30.57, 28.81, 24.14.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A compound having the formula:

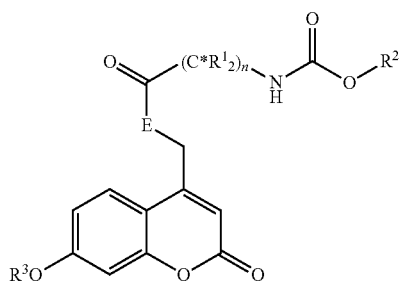

wherein:
 each $R^1$ is independently H or D;
 $R^2$ is alkyl or cycloalkyl;
 $R^3$ is a H, alkyl, cycloalkyl, heterocycloalkyl, or carboxylate;
 E is $NR^4$;
 $R^4$ is H or alkyl;
 n is an integer from 1 to 20; and
 C* represents a natural distribution of $^{12}C$ and $^{13}C$, or enrichment with $^{13}C$.

2. The compound of claim 1, wherein E is NH.

3. The compound of claim 1, wherein $R^3$ is a heterocycloalkyl group of formula:

wherein:
 $R^5$ and $R^6$ are each independently —OH, —CO(O)X, or —OSO$_3$X; and
 X is H, Li$^+$, Na$^+$, K$^+$, or [NR$^4$]$^+$.

4. The compound of claim 3, $R^5$ is OH and $R^6$ is OH.

5. The compound of claim 3, wherein $R^5$ is —CO(O)X, $R^6$ is —OSO$_3$X, and X is H.

6. The compound of claim 3, wherein $R^5$ is —CO(O)H and $R^6$ is OH.

7. The compound of claim 1, wherein $R^2$ is a C$_3$-C$_6$ alkyl.

8. The compound of claim 1, wherein n is an integer from 2 to 12.

9. The compound of claim 1, wherein $R^3$ is H and n is 3.

10. The compound of claim 1, which is:

or wherein m is 3 or 4.

11. A method for assaying α-L-iduronidase enzymatic activity, comprising:
 contacting an α-L-iduronidase substrate with α-L-iduronidase for a pre-determined time to provide a solution comprising an α-L-iduronidase product;

contacting the α-L-iduronidase with an α-L-iduronidase internal standard before, simultaneously with, or after contacting the α-L-iduronidase substrate with α-L-iduronidase to provide a solution comprising, the α-L-iduronidase product and α-L-iduronidase internal standard, extracting the solution comprising the α-L-iduronidase product and α-L-iduronidase internal standard with an organic solvent to provide an organic phase that includes the α-L-iduronidase product and α-L-iduronidase internal standard; and determining the quantity of the α-L-iduronidase product; wherein the internal standard has the formula:

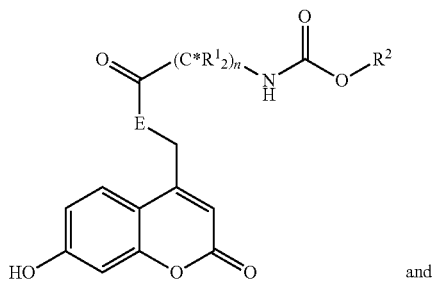

and the substrate has the formula:

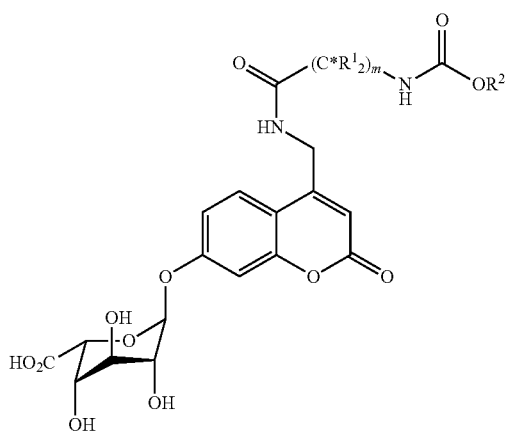

wherein:
each $R^1$ is independently H or D;
$R^2$ is, alkyl or cycloalkyl;
E is $NR^4$ or O;
$R^4$ is H or alkyl; and
m is an integer from 1 to 20;
n is an integer from 1 to 20.

12. The method of claim 11, wherein n is an integer from 2 to 12.

13. The method of claim 11, wherein the solution comprising α-L-iduronidase is obtained by contacting a sample containing α-L-iduronidase with a first buffer solution.

14. The method of claim 11, wherein the α-L-iduronidase substrate is a blood sample.

15. The method of claim 14, wherein the blood sample is a dried blood spot from a newborn screening card.

16. The method of claim 11, wherein in is an integer from 2 to 12.

17. The method of claim 11, wherein $R^2$ is isopropyl or tert-butyl.

18. The method of claim 11, wherein in is an integer from 2 to 20 and n is equal to m minus 1 (m−1).

19. A mixture comprising an internal standard and a substrate, wherein the internal standard has the formula:

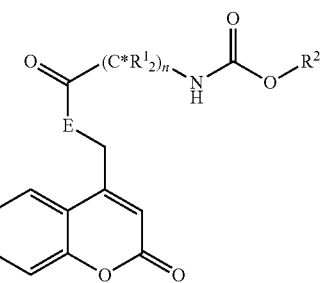

and the substrate has the formula:

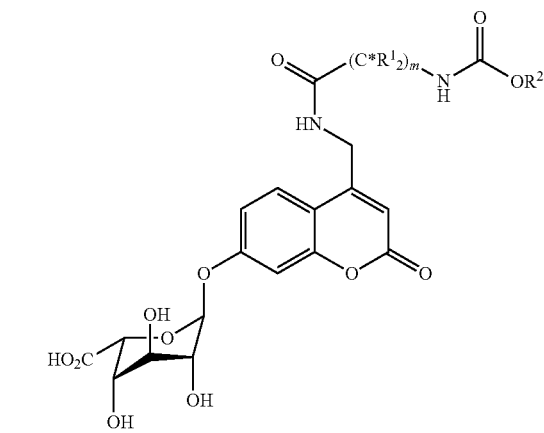

wherein:
each $R^1$ is independently H or D;
$R^2$ is alkyl or cycloalkyl;
E is $NR^4$ or O;
$R^4$ is H or alkyl; and
in is an integer from 1 to 20;
n is an integer from 1 to 20.

* * * * *